United States Patent
Suyanto

(10) Patent No.: US 10,786,442 B2
(45) Date of Patent: Sep. 29, 2020

(54) TOPICAL COMPOSITION FOR REDUCING AGE SPOTS AND WRINKLES

(71) Applicant: Wicky Suyanto, Coto de Caza, CA (US)

(72) Inventor: Wicky Suyanto, Coto de Caza, CA (US)

(*) Notice: Subject to any disclaimer, the term of this patent is extended or adjusted under 35 U.S.C. 154(b) by 0 days.

(21) Appl. No.: 16/058,864

(22) Filed: Aug. 8, 2018

(65) Prior Publication Data

US 2020/0046630 A1   Feb. 13, 2020

(51) Int. Cl.
- *A61K 8/9789* (2017.01)
- *A61K 8/98* (2006.01)
- *A61Q 19/08* (2006.01)
- *A61K 8/55* (2006.01)
- *A61Q 19/02* (2006.01)
- *A61K 8/35* (2006.01)

(52) U.S. Cl.
CPC ............ *A61K 8/9789* (2017.08); *A61K 8/355* (2013.01); *A61K 8/55* (2013.01); *A61K 8/98* (2013.01); *A61Q 19/02* (2013.01); *A61Q 19/08* (2013.01)

(58) Field of Classification Search
CPC . A61K 8/355; A61K 8/55; A61K 8/64; A61K 8/9789; A61K 8/98; A61K 8/982; A61Q 19/02; A61Q 19/08
See application file for complete search history.

(56) References Cited

U.S. PATENT DOCUMENTS

| | | | |
|---|---|---|---|
| 2004/0166069 A1* | 8/2004 | Gupta | A61K 8/675 424/59 |
| 2006/0018867 A1* | 1/2006 | Kawasaki | A61K 8/898 424/70.122 |
| 2011/0014141 A1* | 1/2011 | Nakayama | A61K 8/0208 424/62 |

FOREIGN PATENT DOCUMENTS

| | | | | |
|---|---|---|---|---|
| JP | 2006249045 A | * | 9/2006 | |
| WO | WO-2016090247 A1 | * | 6/2016 | A61K 8/34 |

OTHER PUBLICATIONS

Mohammadi Nafchi, et al (International Journal of Biological Macromolecules, 2013, vol. 62, pp. 397-404) (Year: 2013).*
JP-2006249045-A, Espacenet English Translation, downloaded Nov. 2019 (Year: 2019).*
Lloyd, Suyanto (the applicant), et al (Journal of Clinical and Experimental Dermatology Research, Jun. 2017, 14th International Conference on Clinical and Experimental Dermatology Abstract) (Year: 2017).*

* cited by examiner

Primary Examiner — Mark V Stevens

(57) ABSTRACT

A topical composition for treating age spots and wrinkles includes at least one first skin-whitening agent, at least one wrinkle-reducing agent, and a pharmaceutically or cosmetically acceptable solvent. In a preferred embodiment, the composition includes two whitening agents and two wrinkle-reducing agents. The skin-whitening agents include a tyrosinase-inhibiting glycosylated hydroquinone and a blend of alpine plant-based extracts. The wrinkle-reducing agents include avian egg extract and stabilized vitamin C.

2 Claims, 2 Drawing Sheets

TOPICAL COMPOSITION FOR REDUCING AGE SPOTS AND WRINKLES

FIELD OF THE INVENTION

The present disclosure relates in general to skin care compositions and more particularly to a topical composition for reducing age spots and wrinkles.

BACKGROUND

Human skin changes with age. It becomes thinner, losing some of the smoothness and pleasant plumpness that makes younger skin aesthetically pleasing. These changes become more drastic with exposure to sunlight, which causes the skin to lose elasticity and eventually, to sag and wrinkle. In addition, the sun can cause excess production of melanin, leading to small dark spots on the skin, known as age spots, liver spots, or solar lentigines.

A multitude of skincare products claim to prevent or reduce the effects of aging skin. For instance, there are numerous moisturizers that combat dryness and make wrinkles less noticeable. There also many skin whiteners available for reducing age spots. However, there are few, if any, products that are clinically proven to remove both wrinkles and age spots. Furthermore, many skin care products can cause side effects such as redness, flakiness, peeling, and increased sensitivity to sunlight.

The present disclosure addresses these problems as described below.

SUMMARY OF THE INVENTION

Briefly, a topical composition according to the present disclosure comprises a solvent, at least one skin-whitening agent dissolved in the solvent, and at least one wrinkle-reducing agent dissolved in the solvent. In a preferred embodiment, the solvent is water, and both skin-whitening agent and the wrinkle-reducing agent are water soluble.

In one aspect of the disclosure, the wrinkle-reducing agent comprises egg protein. Preferably, the egg protein is in the form of a fertilized avian egg extract containing Platelet-Derived Growth Factor (PDGF-BB), Transforming Growth Factor β-1 (TGF β-1), and Lysyl Oxidase (LOX). The fertilized avian egg extract is preferably present in the range of about 0.01% to about 3% of the total composition.

In another aspect of the disclosure, the wrinkle-reducing agent comprises a stabilized form of vitamin C. The vitamin C is preferably a sodium salt of the monophosphate ester monophosphate ester of ascorbic acid having the structure

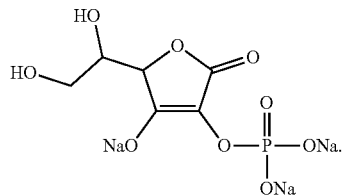

In still another aspect of the disclosure, the at least one wrinkle-reducing agent comprises a first wrinkle-reducing agent comprising fertilized avian egg extract and a second wrinkle-reducing agent comprising stabilized vitamin C.

In yet another aspect of the disclosure, the at least one skin-whitening agent comprises a blend of alpine plant-based extracts including Primula veris extract, Alchemilla vulgaris extract, Veronica officinalis extract, Melissa officinalis leaf extract, Achilliea mille folium extract, and combinations thereof.

In another aspect of the disclosure, the at least one skin-whitening agent comprises a tyrosinase-inhibiting glycosylated hydroquinone. The tyrosinase-inhibiting glycosylated hydroquinone preferably comprises arbutin. More preferably, the tyrosinase-inhibiting glycosylated hydroquinone comprises alpha arbutin.

In another aspect of the disclosure, the at least one skin-whitening agent comprises a first skin whitening agent including a blend of alpine plant-based extracts and a second skin whitening agent including a tyrosinase-inhibiting glycosylated hydroquinone. The first skin-whitening agent is preferably present in the present in the range of about 1% to about 5% of the total composition; and the second skin-whitening agent is present in the range of about 0.01% to about 3% of the total composition.

In still another aspect of the disclosure, the composition includes about 85% to about 89% solvent, about 1% to about 13% vitamins, about 1% to about 15% emollients, about 0.13% to about 7% humectants, 0.3% to about 1% moisturizers, 0.005% to about 15% antioxidants, about 0.001% to about 0.1% preservatives, 0.005 to 1.0% gelling agent, and 0.005% to 1% natural fragrance.

In the above aspect, the vitamins preferably include about 1.0% to about 2.99% sodium ascorbyl phosphate (vitamin C) and about 0.001% to about 10% tocopheryl acetate (vitamin E acetate).

The antioxidants are preferably selected from the group comprising ubiquinone (CoQ10), Vaccinium macrocarpon (cranberry) fruit extract, punica, granatum (pomegranate) extract, Vaccinium angustifolium (blueberry) extract, Fragaria vesca (strawberry) fruit extract, Actinidia chinensis (kiwi) extract, ferulic acid, and combinations thereof. More preferably, the antioxidants comprise a blend including equal parts Vaccinium macrocarpon (cranberry) fruit extract, punica, granatum (pomegranate) extract, Vaccinium angustifolium (blueberry) extract, Fragaria vesca (strawberry) fruit extract, Actinidia chinensis (kiwi) extract, and Helianthus annuus (sunflower) seed oil. The blend may also include ubiquonone and ferulic acid.

In yet another aspect of the disclosure, the composition comprises humectants including egg protein, glycerin, Glycereth-2 Cocoate, and sodium hyaluronate acid. The egg protein preferably comprises a fertilized avian egg extract that contains Platelet-Derived Growth Factor (PDGF-BB), Transforming Growth Factor β-1 (TGF β-1), and Lysyl Oxidase (LOX).

In another aspect of the disclosure, a method of formulating a serum for treating wrinkles and age spots in human skin comprises: creating a mixture comprising a solvent, a gelling agent, antioxidants, a moisturizer, humectants, and emollients; adding a first skin-whitening agent comprising a blend of alpine plant-based extracts into the mixture and mixing until uniform; and adding a second skin-whitening agent including a glucoside into the mixture and mixing until uniform. The method preferably also includes adding avian egg extract and stabilized vitamin C to the mixture before adding the first and second skin-whitening agents.

In still another aspect of the disclosure, a method of treating wrinkles and age spots in a human comprises applying on the skin of the individual a safe and effective amount of a composition including a solvent, first and second skin-whitening agents, and first and second wrinkle-reducing agents, wherein the solvent is in the range of about 85% to about 89% of the total composition, the first skin-whitening agent is in the range of about 1% to about 5% of the total composition, and the second skin-whitening agent is in the range of about 0.01 to 3.0% of the total composition, the first wrinkle-reducing agent is in the range of about 0.01 to 3% of the total composition, and the second wrinkle-reducing agent is in the range of about 1.0% to about 2.99% of the total composition.

DETAILED DESCRIPTION

Figure 1:
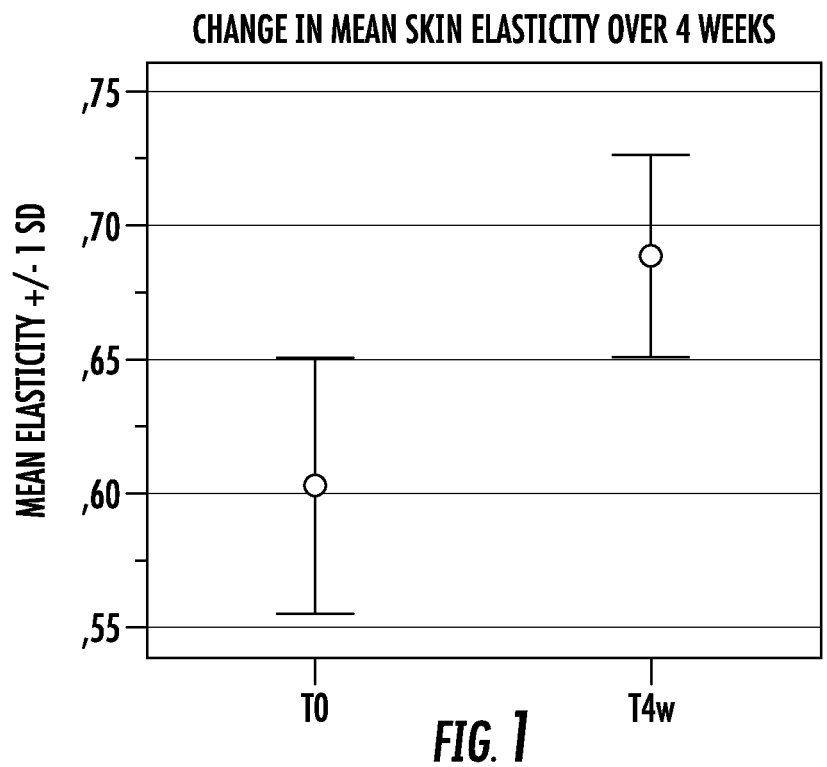
FIG. 1 is a graph depicting the change in mean skin elasticity over 4 weeks for subjects treated with a composition according to the present disclosure.

As required, detailed embodiments of the present invention are disclosed herein; however, it is to be understood that the disclosed embodiments are merely exemplary of the invention that may be embodied in various and alternative forms. Therefore, specific structural and functional details disclosed herein are not to be interpreted as limiting, but merely as a representative basis for teaching one skilled in the art to variously employ the present invention.

The present disclosure describes a topical composition for treating wrinkles and age spots in human skin, and a method of formulating the composition. The composition includes at least one skin-whitening agent, at least one wrinkle-reducing agent, and a pharmaceutically or cosmetically acceptable solvent. In a preferred embodiment, the at least one skin-whitening agent comprises a first skin-whitening agent comprising a water-soluble blend of tyrosinase-inhibiting plant-based extracts and a second skin-whitening agent comprising a tyrosinase-inhibiting glycosylated hydroquinone. The at least one wrinkle-reducing agent preferably comprises a first wrinkle-reducing agent comprising avian egg protein and a second wrinkle-reducing agent comprising stabilized vitamin C. To the best of this inventor's knowledge, neither avian egg protein nor stabilized vitamin C have previously been recognized as wrinkle-reducing agents.

The first skin whitening agent, which is preferably present in the range of about 1% to about 5%, or more preferably about 1.25% to about 4.46%, of the total composition, is preferably a blend of tyrosinase-inhibiting agents selected from the group of alpine plant-based extracts comprising Primula veris extract, Alchemilla vulgaris extract, Veronica officinalis extract, Melissa officinalis leaf extract, and Achilliea mille folium extract. The blend may be obtained in the form of the product sold under the trade name GIGAWHITE™ by DSM Nutritional Products Europe, Basel, Switzerland, which contains all the above extracts, as well as Malva sylvestris (mallow) extract, which serves as an anti-irritant, and Mentha piperita (peppermint) extract, which serves as a calming agent.

The second skin whitening agent, which is preferably present in the range of about 0.01 to 3.0% of the total composition, preferably comprises a tyrosinase-inhibiting glycosylated hydroquinone such as arbutin. More preferably, the second skin whitening agent comprises alpha arbutin (chemical name: 4-hydroxyphenyl-D-lucopyranoside), which is available from DSM Nutritional Products, Parsippany, N.J.

The first wrinkle-reducing agent preferably comprises egg protein in the form of a fertilized avian egg extract that contains Platelet-Derived Growth Factor (PDGF-BB), Transforming Growth Factor β-1 (TGF β-1), and a natural matrix cross-linker, Lysyl Oxidase (LOX), and does not contain metabolic steroid hormones or major kinases. One suitable avian egg extract meeting these requirements is the product LPAE (LifePharm Inc., Lake Forest, Calif.), which is prepared from eggs of chickens fed high-quality grains and not exposed to any chemicals. The fertilized avian egg extract is preferably present in the range of about 0.01% to about 3% of the total composition.

The second wrinkle-reducing agent comprises a stabilized form of vitamin C. The vitamin C is preferably a sodium salt of the monophosphate ester of ascorbic acid having the structure shown in Table 1. This stable form of the vitamin is available under the trademark STAY-C® 50 from DSM Nutritional Products, Parsippany, N.J.

TABLE 1

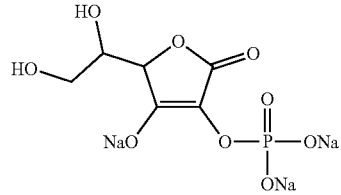

The composition may also include one or more of vitamins, emollients, humectants, moisturizers, antioxidants, anti-irritants, calming agents, anti-inflammatories, preservatives, gelling agents, anti-inflammatories, skin conditioners, and fragrance. In a preferred embodiment, the composition includes about 85% to about 89% solvent, about 1% to about 13% vitamins, about 1% to about 15% emollients, about 0.13% to about 7% humectants, 0.3% to about 1% moisturizers, 0.005% to about 15% antioxidants, about 0.001% to about 0.1% preservatives, 0.005 to 1.0% gelling agent, and 0.005% to 1% natural fragrance.

In addition to the stabilized vitamin C described above, which is present in the range of about 1.0% to about 2.99% of the total composition, the vitamins preferably include tocopheryl acetate (vitamin E acetate) in the range of about 0.001% to about 10% of the total composition.

The antioxidants may be selected from the group comprising ubiquinone (CoQ10), Vaccinium macrocarpon (cranberry) fruit extract, punica, granatum (pomegranate) extract, Vaccinium angustifolium (blueberry) extract, Fragaria vesca (strawberry) fruit extract, Actinidia chinensis (kiwi) extract, ferulic acid, and combinations thereof. In a preferred embodiment, the composition includes ubiquonone, ferulic acid, and an antioxidant blend known as VPF-1359, which comprises equal parts Vaccinium macrocarpon (cranberry) fruit extract, punica, granatum (pomegranate) extract, Vaccinium angustifolium (blueberry) extract, Fragaria vesca (strawberry) fruit extract, Actinidia chinensis (kiwi) extract, and Helianthus annuus (sunflower) seed oil.

The humectants may be selected from the group comprising the above-described egg protein, glycerin, Glycereth-2 Cocoate, sodium hyaluronate acid, and combinations thereof. In a preferred embodiment, the composition includes all four of the humectants in this group.

The emollients may be selected from the group comprising aloe barbadensis leaf juice, butylene glycol, propanediol, Helianthus annuus (sunflower) seed oil, and combinations thereof. The moisturizer may comprise ethylhexylglycerin. The preservatives may be selected from the group comprising phenoxyethanol, benzoic acid, and combinations thereof. The gelling agent may comprise carbomer (Carbopol 980). The fragrance may comprise citrus Aurantium dulcis (orange) peel oil.

The composition may be formulated by a five-phase process. In the first phase, solvent, a first emollient, a gelling agent, and a first antioxidant are mixed in a main tank using a turbine mixer and a side sweeper. The first antioxidant is preferably a skin conditioner such as ubiquinone (CoQ10). The ingredients are then mixed with a high shear mixer. In the second phase, second and third emollients, a first moisturizer, and first and second humectants are pre-mixed and then added to the main tank. One of the humectants is preferably a skin-conditioner such as sodium hyaluronate acid. In the third phase, a third humectant is mixed in with the other ingredients in the tank. In the fourth phase, a first vitamin is premixed with deionized water, and the premixture is added to the main tank. In the fifth phase, first and second whitening agents, a second antioxidant, a second vitamin, an anti-oxidant blend, and a preservative mixture are added to the tank and mixed for a predetermined amount of time. The preservative mixture preferably also includes a second moisturizer and a fourth humectant. For instance, the product manufactured under the trademark Lincoserve™ PE955 by Lincoln Fine Ingredients, Lincoln, R.I., which includes the preservatives pheoxyethanol and benzoic acid as well as the moisturizer ethylhexylglycerin and the humectant glycereth-2 cocoate, may be used.

EXAMPLES

TABLE 2

| Name of the Ingredients | % Range | Function |
| --- | --- | --- |
| Water(Aqua) | 85-89 | Solvent |
| Aloe Barbadensis Leaf Juice | 0.100-0.500 | Emollient |
| Butylene Glycol | 1.0-3.0 | Emollient |
| Malva Sylvestris (mallow) Extract | .01-1.0 | Anti-irritant |
| Mentha Piperita (peppermint) Leaf Extract | 0.05-0.5 | Calming agent |
| Primula Veris Extract | 0.05-0.5 | Lighting Whitening, Anti-aging |
| Alchemilla Vulgaris Extract | 0.30-0.99 | Lighting Whitening, Anti-aging |
| Veronica Officinalis Extract | 0.30-0.99 | Lighting Whitening, Anti-aging |
| Melissa Officinalis Leaf Extract | 0.30-0.99 | Lighting Whitening, Anti-aging |
| Achillea Millefolium Extract | 0.30-0.99 | Lighting Whitening, Anti-aging |
| Sodium Ascorbyl Phosphate (Vitamin C) | 1.0-2.99 | Vitamin, Wrinkle reduction |
| LFAE Protein (Egg Protein) | .01-3.0 | Humectant, Wrinkle reduction |
| Alpha Arbutin | .01-3.0 | Lighting Whitening, Anti-aging |
| Phenoxyethanol | 0.1 | Preservative |
| Benzoic Acid | .001-0.10 | Preservative |
| Ethylhexylglycerin | .001-0.01 | Moisturizer |
| Glycereth-2 Cocoate | 0.01-2.0 | Humectant |
| Methyl Gluceth 20 | .30-.99 | Moisturizer |
| Glycerin | 0.1-1.0 | Humectant |

TABLE 2-continued

| Name of the Ingredients | % Range | Function |
| --- | --- | --- |
| Propanediol | 0.001-1.0 | Emollient |
| Carbomer | 0.005-1.0 | Gelling Agent |
| Citrus Aurantium Dulcis (Orange) Peel Oil | 0.01-1.0 | Natural Fragrance |
| Ubiquinone (CoQ10) | 0.01-1.0 | Antioxidant, Skin conditioner |
| Sodium Hyaluronate Acid | 0.01-1.0 | Humectant, Skin conditioner |
| Tocopheryl Acetate (Vitamin E Acetate) | 0.001-10 | Vitamin |
| Helianthus Annuus (Sunflower) Seed Oil | 0.001-10 | Emollient |
| Vaccinium Macrocarpon (Cranberry) Fruit Extract | 0.001-10 | Antioxidant, anti-inflammatory |
| Punica Granatum Extract | 0.001-10 | Antioxidant |
| Vaccinium Angustifolium (Blueberry) Extract | 0.001-10 | Antioxidant |
| Fragaria Vesca (Strawberry) Fruit Extract | 0.001-10 | Antioxidant |
| Actinidia Chinensis (Kiwi) Extract | 0.001-10 | Antioxidant |
| Ferulic Acid | 0.0001-0.02 | Antioxidant |

Example 1

A serum having the ingredients in the percentages shown in Table 2 was prepared as follows:

Phase 1

Step 1: Water was added to a main tank, with a turbine mixer started at 50-70% capacity and a side sweeper at maximum capacity.

Step 2: Aloe Vera 200× Powder was added while mixing. Mixing continued for 1-3 minutes.

Step 3. Carbopol 980 was added while mixing. Mixing continued for 1-3 minutes.

Step 4. CoQ10 was added while mixing. Mixing continued for 1-3 minutes.

Step 5. A high shear mixer was started at 50-70% capacity. Mixing continued 20-30 minutes.

Step 6. The high shear mixer was stopped.

Phase 2

Step 7. In a stainless-steel kettle, Butylene Glycol, Sodium Hyaluronic Acid, Methyl Gluceth 20, Glycerin, and propanediol (Zemea) were premixed in a stainless-steel kettle at low speed.

Step 8. The premix was added directly to the main tank.

Phase 3

Step 9. Fertilized avian Egg Extract (LFAE protein) was slowly sprinkled directly into to the main tank with mixing speed 50-70%.

Phase 4

Step 10. Deionized water and Sodium Ascorbyl Phosphate were premixed in a stainless-steel kettle until clear and all powder dissolved.

Step 11. The premix was added directly to main tank with mixing speed at 50-70%.

Phase 5

Step 12. Giga White, Ferulic Acid, Orange Sweet Oil, Vitamin E, a blend of anti-oxidants (VPF-1359), Lincoserve PE955, and Alpha Arbutin were added directly to the main tank with mixing speed at 50-70%.

Step 13. The ingredients were mixed until uniform between each addition.

Step 14. The pH of serum was checked and confirmed to be within a target pH range of 5.5-6.5.

Example 2

A study was undertaken to evaluate the tolerability of a serum having ingredients in the ranges shown in Table 1 and formulated according to the method described in Example 1. Test subjects consisted of 20 healthy females aged 40 years and older with crow's feet next to the eyes and age spots on neck and upper chest. Exclusion criteria included: severe or chronic skin inflammation; serious inner or chronic diseases; intake of drugs that possibly can interfere with skin reactions (Glucocorticoids, antiallergics, topical immuno modulator, etc.); application of pharmaceutical products and skin care products with active ingredients until 7-10 days before testing; severe allergies or occurrence of severe side effects after usage of cosmetic products; sunbath or usage of tanning bed during the study period; known cancer; pregnancy or lactation period. The subjects were instructed to apply the serum twice daily (in the morning after cleansing and in the evening while sleeping) for a period of four weeks.

At the beginning of the study, all study participants were determined to have healthy skin by dermatological standard and criteria. No pathological skin disorder was detected. No complaint of any pathological skin disorder was reported during the test. Interruptions of test and/or medical intervention were not necessary. During the final dermatological examination at the end of the study, none of the participants showed development of any pathological skin disorder. The serum was well-tolerated, no evidence of any pathological skin disorder could be detected. It was concluded that the use of the product in practice does not lead to any undesired skin reactions due to skin irritant or sensitizing characteristics of the product.

Example 3

Age spots in the twenty subjects in the study of Example 2 were examined using spectrophotometry before and after the 4-week study period. The color of the age spots was evaluated using the L*a*b* color space, as standardized in the EN ISO 11664-4. Measurements were taken of L*, a*, b*, and individual topology angle (ITA°) values for each spot, where L* represents brightness, a* represents red-green-coloration, b* represents blue-yellow coloration, and ITA° is a vector representation in the plane of L* vs. b*, defined as ITA°=(arctan(L*−50/b))×180/n. An increase in skin tanning of pigmentation spots can be basically described by an increased b* and a decreased L* value. A bleaching effect should be marked by a decreased b* and an increased L* value. A increasing a* value corresponds an augmentation in skin redness, thus it can be disregarded for the characterization of a bleaching effect. The brighter the pigmentation spot the higher is the ITA° values. Hence, a bleaching effect is characterized by an increased ITA° value.

The L* values for each study participant before and after the 4-week period are shown in Table 3. The average L* value for the participants increased by 7.4%.

TABLE 3

Change in L* value over 4 weeks

| Subjects | Before | After 4 weeks | Difference | Rel. Change in % |
|---|---|---|---|---|
| 1. | 53.36 | 56.28 | 2.93 | 5.48 |
| 2. | 56.75 | 60.41 | 3.66 | 6.45 |
| 3. | 55.32 | 60.19 | 4.87 | 8.79 |
| 4. | 57.50 | 61.34 | 3.84 | 6.67 |
| 5. | 55.00 | 60.59 | 5.59 | 10.16 |
| 6. | 56.55 | 55.15 | −1.40 | −2.48 |
| 7. | 54.98 | 58.25 | 3.27 | 5.94 |
| 8. | 59.32 | 62.57 | 3.26 | 5.49 |
| 9. | 56.19 | 61.40 | 5.21 | 9.26 |
| 10. | 58.10 | 61.35 | 3.25 | 5.59 |
| 11. | 54.25 | 63.08 | 8.83 | 16.27 |
| 12. | 55.56 | 59.28 | 3.73 | 6.71 |
| 13. | 58.50 | 64.06 | 5.56 | 9.51 |
| 14. | 54.87 | 60.33 | 5.46 | 9.94 |
| 15. | 58.37 | 57.92 | −0.45 | −0.78 |
| 16. | 57.55 | 60.58 | 3.03 | 5.26 |
| 17. | 56.45 | 60.04 | 3.59 | 6.36 |
| 18. | 54.46 | 59.97 | 5.51 | 10.12 |
| 19. | 54.97 | 58.46 | 3.50 | 6.36 |
| 20. | 59.33 | 69.35 | 10.03 | 16.90 |
| Average | 56.37 | 60.53 | 4.16 | 7.40 |
| Minimum | 53.36 | 55.15 | −1.40 | −2.48 |
| Maximum | 59.33 | 69.35 | 10.33 | 16.90 |
| Stand. Deviation | 1.76 | 2.98 | 2.55 | 4.51 |

The a* values for each study participant before and after the 4-week period are shown in Table 4. The average a* value for the participants decreased by 3.05%.

TABLE 4

Change in a* value over 4 weeks

| Subjects | Before | After 4 weeks | Difference | Rel Change in % |
|---|---|---|---|---|
| 1. | 8.26 | 9.58 | 1.32 | 15.92 |
| 2. | 9.22 | 11.30 | 2.08 | 22.51 |
| 3. | 10.19 | 9.48 | −0.72 | −7.02 |
| 4. | 9.07 | 7.87 | −1.20 | −13.24 |
| 5. | 9.89 | 7.16 | −2.73 | −27.62 |
| 6. | 10.65 | 10.35 | −0.30 | −2.82 |
| 7. | 13.34 | 14.62 | 1.28 | 9.56 |
| 8. | 9.18 | 9.98 | 0.81 | 8.77 |
| 9. | 7.52 | 6.70 | −0.82 | −10.97 |
| 10. | 12.14 | 12.28 | 0.14 | 1.15 |
| 11. | 12.06 | 6.20 | −5.86 | −48.59 |
| 12. | 11.81 | 11.73 | −0.08 | −0.72 |
| 13. | 9.77 | 10.08 | 0.32 | 3.23 |
| 14. | 9.64 | 9.78 | 0.14 | 1.45 |
| 15. | 9.35 | 8.46 | −0.90 | −9.57 |
| 16. | 6.96 | 7.80 | 0.85 | 12.15 |
| 17. | 10.80 | 8.58 | −2.23 | −20.60 |
| 18. | 8.36 | 8.71 | 0.35 | 4.19 |
| 19. | 10.90 | 10.37 | −0.54 | −4.91 |
| 20. | 5.20 | 5.52 | 0.32 | 6.16 |
| Average | 9.71 | 9.32 | −0.39 | −3.05 |
| Minimum | 5.20 | 5.52 | −5.86 | −48.59 |
| Maximum | 13.34 | 14.62 | 2.08 | 22.51 |
| Stand. Deviation | 1.93 | 2.20 | 1.73 | 16.18 |

The b* values for each study participant before and after the 4-week period are shown in Table 5. The average b* values for the participants decreased by 5.67%. This indicates that the serum caused a reduction in the pigmentation of age spots.

TABLE 5

Change in b* value over 4 weeks

| Subjects | Before | After 4 weeks | Difference | Rel. Change in % |
|---|---|---|---|---|
| 1. | 18.46 | 16.96 | −1.50 | −8.15 |
| 2. | 17.84 | 16.35 | −1.49 | −8.35 |
| 3. | 17.52 | 13.34 | −4.19 | −23.89 |
| 4. | 19.32 | 17.19 | −2.13 | −11.00 |
| 5. | 19.69 | 17.98 | −1.71 | −8.69 |
| 6. | 18.64 | 18.52 | −0.13 | −0.67 |
| 7. | 16.38 | 16.08 | −0.30 | −1.86 |
| 8. | 18.07 | 14.94 | −3.14 | −17.35 |
| 9. | 18.04 | 18.02 | −0.02 | −0.11 |
| 10. | 12.73 | 11.20 | −1.53 | −11.98 |
| 11. | 15.71 | 17.93 | 2.22 | 14.10 |
| 12. | 18.43 | 19.26 | 0.83 | 4.50 |
| 13. | 17.01 | 18.72 | 1.71 | 10.05 |
| 14. | 18.61 | 16.95 | −1.66 | −8.92 |
| 15. | 17.49 | 18.03 | 0.54 | 3.09 |
| 16. | 19.04 | 17.86 | −1.18 | −6.20 |
| 17. | 20.12 | 20.69 | 0.57 | 2.86 |
| 18. | 18.82 | 19.25 | 0.43 | 2.26 |
| 19. | 18.05 | 13.37 | −4.68 | −25.93 |
| 20. | 16.81 | 13.93 | −2.88 | −17.14 |
| Average | 17.84 | 16.83 | −1.01 | −5.67 |
| Minimum | 12.73 | 11.20 | −4.68 | −25.93 |
| Maximum | 20.12 | 20.69 | 2.22 | 14.10 |
| Stand. Deviation | 1.62 | 2.39 | 1.85 | 10.60 |

The ITA° values for each study participant before and after the 4-week period are shown in Table 6. The average ITA° values for the participants increased by 68.61%.

TABLE 6

Change in ITA° value over 4 weeks

| Subjects | Before | After 4 weeks | Difference | Rel. Change in % |
|---|---|---|---|---|
| 1. | 10.30 | 20.32 | 10.02 | 97.31 |
| 2. | 20.72 | 32.48 | 11.76 | 56.79 |
| 3. | 16.89 | 37.37 | 20.48 | 121.25 |
| 4. | 21.22 | 33.40 | 12.18 | 57.39 |
| 5. | 14.24 | 30.49 | 16.25 | 114.16 |
| 6. | 19.35 | 15.53 | −3.82 | −19.73 |
| 7. | 16.91 | 27.15 | 10.24 | 60.57 |
| 8. | 27.27 | 40.09 | 12.81 | 46.99 |
| 9. | 18.94 | 32.31 | 13.37 | 70.59 |
| 10. | 32.48 | 45.38 | 12.90 | 39.73 |
| 11. | 15.14 | 36.11 | 20.97 | 138.53 |
| 12. | 16.78 | 25.73 | 8.95 | 53.37 |
| 13. | 26.54 | 36.90 | 10.36 | 39.04 |
| 14. | 14.66 | 31.35 | 16.68 | 113.76 |
| 15. | 25.58 | 23.71 | −1.87 | −7.32 |
| 16. | 21.63 | 30.64 | 9.01 | 41.66 |
| 17. | 17.77 | 25.87 | 8.11 | 45.64 |
| 18. | 13.33 | 27.39 | 14.05 | 105.42 |
| 19. | 15.38 | 32.32 | 16.94 | 110.17 |
| 20. | 29.03 | 54.26 | 25.23 | 86.94 |
| Average | 19.71 | 31.94 | 12.23 | 68.61 |
| Minimum | 10.30 | 15.53 | −3.82 | −19.73 |
| Maximum | 32.48 | 54.26 | 25.23 | 138.53 |
| Stand. Deviation | 5.84 | 8.63 | 6.82 | 42.04 |

Example 4

Figure 2:
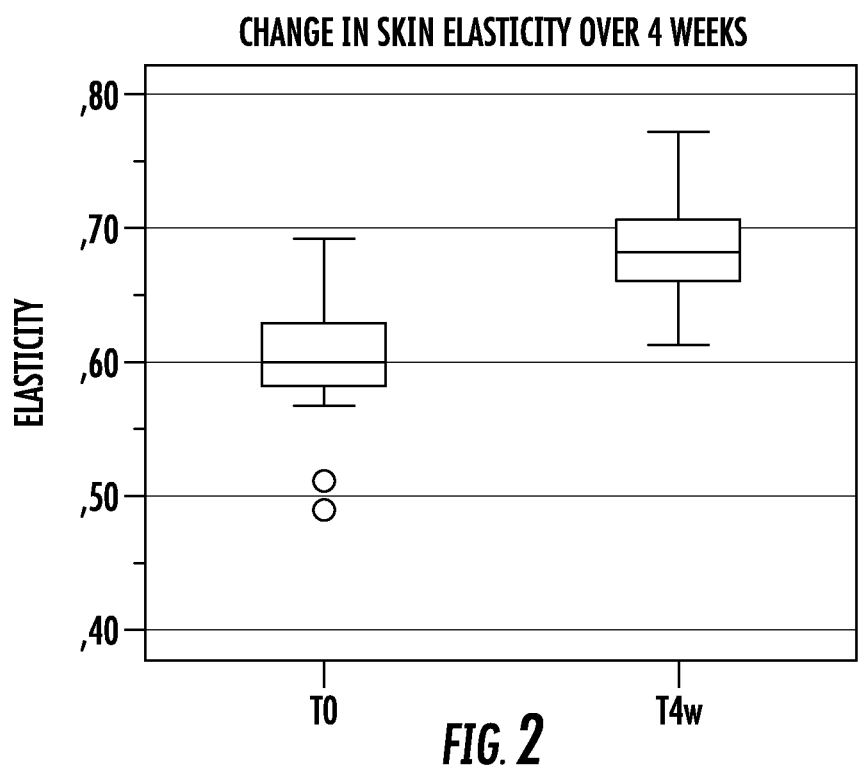
FIG. 2 is a graph depicting the change in skin elasticity over 4 weeks for subjects treated with a composition according to the present disclosure.
Figure 3:
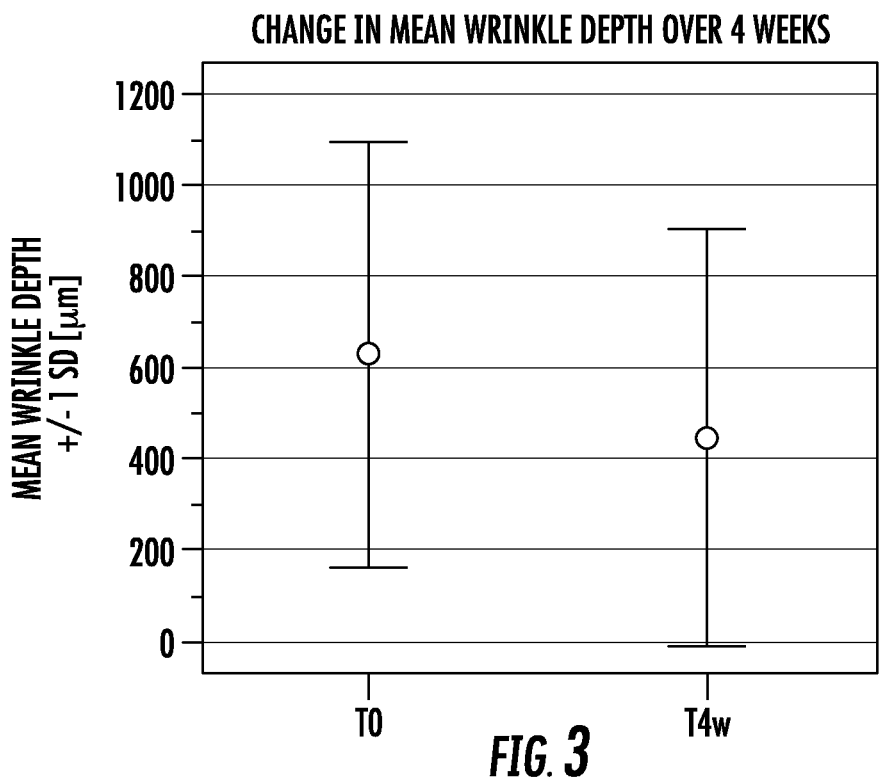
FIG. 3 is a graph depicting the change in mean wrinkle depth over 4 weeks for subjects treated with a composition according to the present disclosure.
Figure 4:
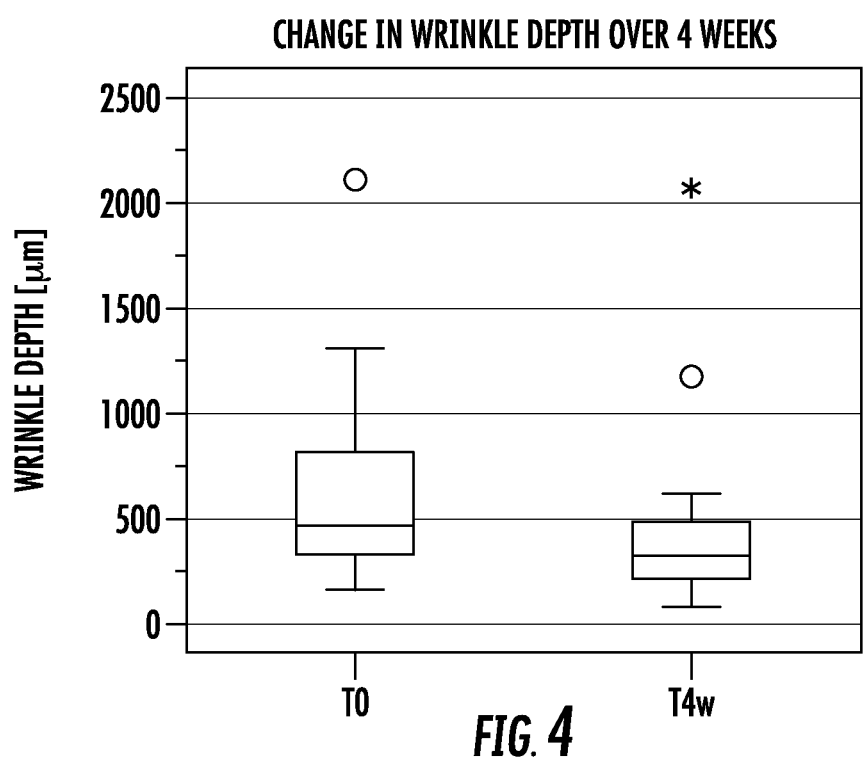
FIG. 4 is a graph depicting the change in wrinkle depth over 4 weeks for subjects treated with a composition according to the present disclosure.

Skin elasticity was measured in the 20 subjects of the study described in Example 2, before and after the 4-week study period. The change in mean elasticity is shown in FIG. 1, and the change in elasticity is shown in FIG. 2. A significant increase in elasticity was shown between the baseline measurement ($T_0$) and the measurement after 4 weeks ($T_{4w}$).

Example 5

Wrinkle depth was measured in the 20 subjects of the study described in Example 2, before and after the 4-week study period. measured in the 20 subjects of the study described in Example 2, before and after the 4-week study period. The change in mean wrinkle depth is shown in Table 9, and the change in wrinkle depth is shown in Table 10. A significant decrease in wrinkle depth was found between the baseline measurement ($T_0$) and the measurement after 4 weeks ($T_{4w}$).

While the principles of the invention have now been made clear in the illustrated embodiment, there may be immediately obvious to those skilled in the art many modifications of structure, arrangements, proportions, elements, materials and components used in the practice of the invention and otherwise, which are particularly adapted for specific environments and operation requirements without departing from those principles. The appended claims are therefore intended to cover and embrace any such modifications within the limits only of the true spirit and scope of the invention.

What is claimed is:

1. A topical formulation for treating wrinkles and age spots in human skin comprising:
    about 85 to about 89% of a solvent comprising water; and
    at least two wrinkle-reducing agents dissolved in the solvent;
    wherein the at least two wrinkle-reducing agents includes 0.01-3% based on the formulation of a fertilized avian egg extract containing Platelet-derived Growth Factor-BB, Transforming Growth Factor beta-1, and Lysyl Oxidase, wherein the fertilized avian egg extract does not contain metabolic steroid hormones, and
    1.0-2.99% of a sodium salt of a monophosphate ester of ascorbic acid having the structure:

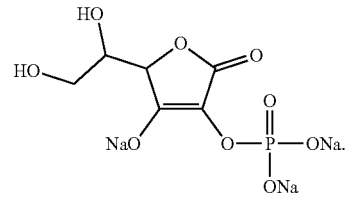

2. A topical formulation for treating wrinkles in human skin comprising:
    about 85 to about 89% of a solvent comprising water;
    a water-soluble wrinkle reducing agent dissolved in the solvent, wherein the water-soluble wrinkle reducing agent comprises 0.01-3% based on the formulation of a fertilized avian egg extract containing Platelet-derived Growth Factor-BB, Transforming Growth Factor-beta 1, and Lysyl Oxidase, wherein the fertilized avian egg extract does not contain metabolic steroid hormones;
    0.3-1% of at least one moisturizer; and
    a gelling agent comprising 0.005-1.0% of the formulation of carbomer.

* * * * *